United States Patent [19]
Rassman

[11] Patent Number: 5,331,472
[45] Date of Patent: Jul. 19, 1994

[54] METHOD AND APPARATUS FOR MEASURING HAIR DENSITY

[76] Inventor: William R. Rassman, 5699 Kanan Rd., #253, Agoura, Calif. 91301

[21] Appl. No.: 944,405

[22] Filed: Sep. 14, 1992

[51] Int. Cl.$^5$ .............................................. G02B 27/00
[52] U.S. Cl. ................................... 359/894; 359/809; 359/808; 359/802
[58] Field of Search ............... 359/798, 800, 801, 802, 359/803, 804, 805, 806, 808, 809, 810, 811, 894

[56] References Cited

U.S. PATENT DOCUMENTS

| | | | |
|---|---|---|---|
| 1,396,607 | 11/1921 | Von Post | 359/798 |
| 2,110,310 | 3/1938 | Shayes et al. | 359/798 |
| 3,981,593 | 9/1976 | Boyle | 359/804 |
| 5,087,112 | 2/1992 | Feinbloom | 359/800 |
| 5,196,964 | 3/1993 | Heine et al. | 359/800 |
| 5,210,647 | 5/1993 | Hartnagel et al. | 359/802 |

*Primary Examiner*—Loha Ben
*Assistant Examiner*—Thomas Robbins
*Attorney, Agent, or Firm*—Fitzpatrick, Cella, Harper & Scinto

[57] ABSTRACT

A method and apparatus for measuring hair in a predefined area of skin. The method addresses the preparation of the skin and the device for counting the hairs in a defined area. The apparatus contains an optical magnifying lens, a housing for the lens and an aperture of known surface area in order to calculate the density of the hair in the portion of skin under measurement. When the method or apparatus are used, the end result will be a density measurement of hair per unit area. When this measurement is compared with similar measurements in the same area from a previous time or from a different area at the same time, a diagnosis of whether hair loss is occurring can be made with considerable accuracy. Similar applications can be made in areas where treatment suggests that hair loss has ceased or reversed through some intervention.

17 Claims, 2 Drawing Sheets

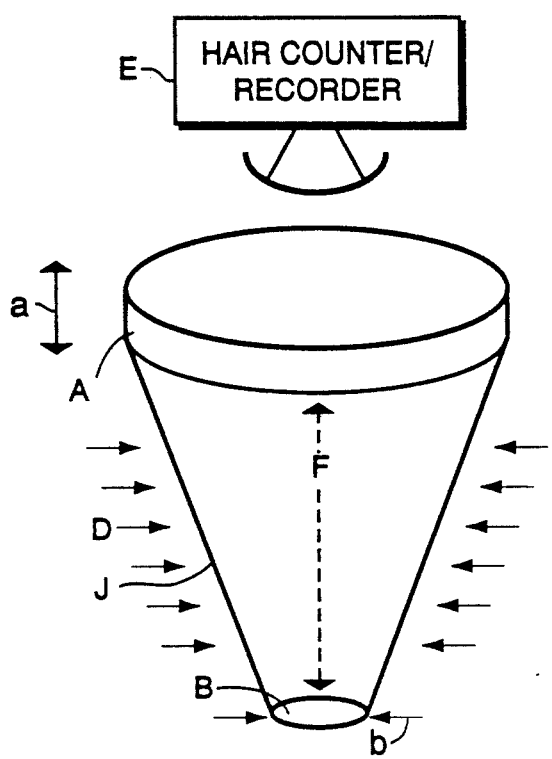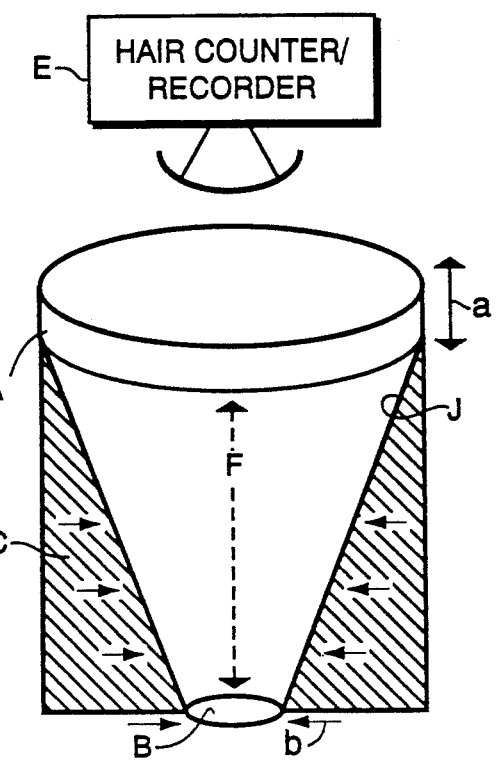
FIG. 1A  FIG. 1B
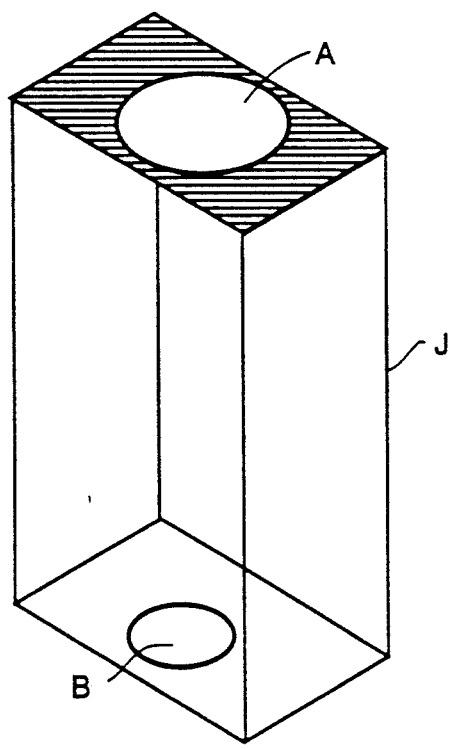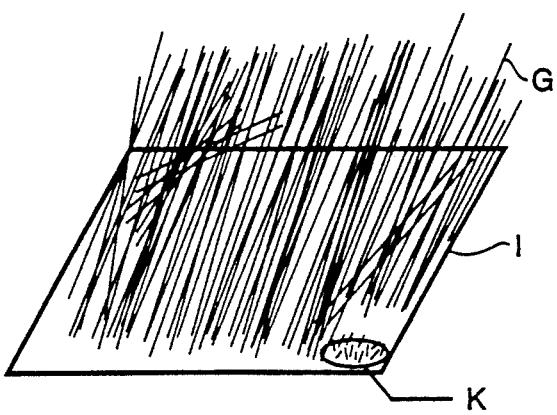
FIG. 1C  FIG. 2

METHOD AND APPARATUS FOR MEASURING HAIR DENSITY

BACKGROUND

1. Field Of The Invention

The present invention is directed to a system which is used to visualize and count the number of human hairs in a visual field. In particular, the invention is directed to a system which is constructed of an optical lens, a chamber to house the lens and an aperture of a fixed or variable size located at the point where the lens is focused.

2. Description of The Related Art

Hair loss is a problem which many men and women experience in their lifetimes. The most common cause of hair loss is associated with a normal aging process. The process of losing ones hair is most often gradual. It is often noticed first during washing or grooming. This observation is imprecise in predicting permanent hair loss as most individual hair follicles go into a dormant period (20% of the hair population at any one time) and a reduction of hair population may be partly the result of this process although this process is usually uniform.

The distinguishing factor which differentiates permanent hair loss from cyclical hair loss is that the population of the hair decreases gradually in affected areas resulting in a permanent loss of hair and a reduction of hair population and hair density. The permanent loss of hair is often selective by anatomical site. In men, hair loss follows one pattern ("Male Pattern Baldness" or "Androgenic Alopecia") and in women it follows another pattern. The process of losing hair also occurs at different rates, for different periods of time and at different ages, even in the same individual.

The ability to diagnose hair loss in its earliest stages is difficult and compounded by many aesthetic factors which reflect the visual contrast between hair color and character against the color background of the scalp. In individuals with black course hair and white skin, the contrast is dramatic and hair loss is evident early in the process. In individuals with blond hair and blond skin, significant hair loss can occur before it is evident as the contrast between scalp and hair color is minimal.

In recent times, various treatments for hair loss have been devised. These treatments take the form of medications, oils or potions which are applied to the scalp to prevent or reverse balding, or surgical procedures which move hair from one part of the scalp to another. In all cases, the diagnosis of hair loss is a subjective assessment made by either doctor or patient, and the response to treatment is often subjective as well. Heretofore, objective measurements of hair density has not been practical and as a result the effectiveness of snake oils of many varieties as well as medicines approved by the Federal Drug Administration go unproven for any selected individual.

SUMMARY OF THE INVENTION

It is an object of the present invention to address the foregoing difficulties.

The invention provides a method and apparatus for visualizing and displaying hair in such a manner that hair density can be obtained by counting hair in a known area under magnification. Hair density is then calculated according to the formula that the hair density for a standard area (x) is equal to the hair count (y) divided by the area studied (z) ($x = y/z$). The hair density can then be compared with the hair density in parts of the scalp that rarely experience hair loss (the back of the head). Such measurements can be spaced over time to understand the changes that occur. The diagnosis of hair loss can therefore be made with scientific precision.

In another aspect, the invention provides a method and apparatus for analyzing the density of permanent (donor) hair used for hair transplantation. Hair transplantation is actually a skin transplant containing quantities of hair which come from portions of the scalp which do not usually experience hair loss. Smaller and smaller transplanted grafts are presently being used. Such smaller grafts are referred to as "Minigrafts". Traditional larger grafts have been sized at 4 or 5 mm and these contain 12+ square mm of skin surface area. The amount of transplanted hair is directly proportional to the measured surface area of the grafts and to the density of the hair in the grafts. A thorough, proper evaluation of the transplantation process requires an assessment of the number of hairs per unit area in the donor site. The need to assess hair density in the donor area is less of a problem with larger grafts than with Minigrafts. In order to accurately assess the number of hairs per unit area that are in the donor area, a device to measure hair density is critical in obtaining predictably high-quality Minigrafts with adequate numbers of hairs. If the hair density of a Minigraft of size "n" has four hairs in Mr. Smith, but three hairs in Mr. Jones, then Mr. Jones will have 25% less hair available from a transplanted graft than Mr. Smith. The end result will be visually less valuable in Mr. Jones than in Mr. Smith given the same hair color and hair characteristics.

This brief summary of the invention is provided so that the nature of the invention may be understood quickly. A fuller understanding may be obtained by reference to the following detailed description of the invention in connection with the appended drawings.

BRIEF DESCRIPTION OF THE DRAWINGS

FIG. 1A is a block diagram showing an embodiment of the invention;

FIG. 1B shows an embodiment of the invention with an internal light source;

FIG. 1C shows an embodiment of the invention with one alternative shape to a cylinder;

FIG. 2 is a view for showing the prepared scalp where the measurement will be taken;

DETAILED DESCRIPTION OF THE PREFERRED EMBODIMENT

An apparatus according to the invention is shown in FIG. 1A. The apparatus includes an optical magnifying lens (A) with adjustable focal length (as indicated by arrow (a)) attached to a hollow cylinder housing (J) at one end, and an aperture (B) at the other end. The optical magnifying lens (A) is set to a focal distance (F) whereby the aperture (B) is in focus. The focal length (F) may be variable or fixed depending upon the optics of the optical magnifying lens (A) and the mechanisms of the attachment to the optical magnifying lens (A). The aperture (B) may be fixed or variable in size depending upon the mechanisms of construction. A diaphragm may be used to control the size of the aperture, and means may be provided for measuring the aperture, as shown at arrows (b). A viewer from (E) may be a human eye, a device which takes a photograph, or a device which counts hairs in aperture (B). A light source (D) indicated by arrows in FIG. 1A may be an external light penetrating the walls of a clear housing (J) in the apparatus or it may be emitted from an internal light source (C) as seen in FIG. 1B. FIG. 1C shows one of many alternate shapes of the apparatus taking the form of a box with lens (A), housing (J) and aperture (B).

FIG. 2 shows a portion of the skin from the scalp of a human head (I), growing hair (G) and hair which is freshly cut (H) close to the skin edge in an area (K) which represents a subset of the scalp area. The size of the area (K) containing the cut hair (H) must be of such a size so as to permit viewing of the hair population with the apparatus demonstrated in FIGS. 1A, 1B, 1C and 3 and through the optical magnifying lens (A).

Figure 3:
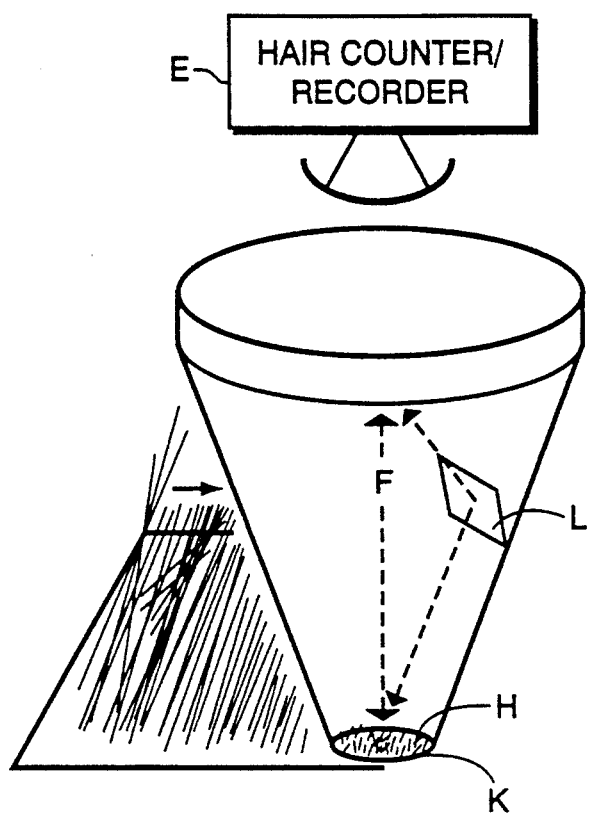
FIG. 3 is a view showing the apparatus placed upon the area to be measured from a lateral (side) view.

FIG. 3 shows the apparatus from FIG. 1A, placed directly upon the area (K) of freshly cut hair (H) so as to view the hair population from the vantage point of the viewer (E) within the cut area (K) of the scalp so that the hair (H) can be counted in the aperture area (B). The focus of lens (A) is adjusted so as to view the area (K) within aperture (B) and the cut hair (H) contained therein.

Figure 4A:
FIG. 4A shows a projected view of the aperture magnified from a lateral (side) view for illustrative purposes.

FIG. 4A shows the area (K) as seen from a side view.

Figure 4B:
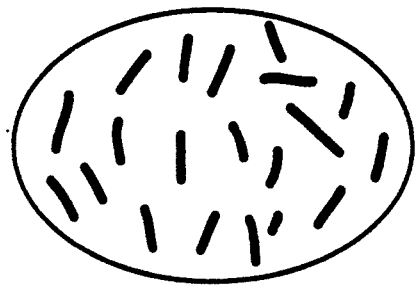
FIG. 4B shows a view of the aperture as seen from the viewing area with the cut hair stubble viewed from the top down.

FIG. 4B is the actual view of area (K) as seen from the viewer's (E) perspective in order to permit a count of the hairs (H) in the area of the aperture (B). If desired, mirrors or sets of mirrors, such as those shown at (L) in FIG. 3, may be provided for viewing aperture (B) from different perspectives.

What is claimed is:

1. A method for measuring hair density, the method comprising the steps of:
    identifying an area of skin from a part of the body for which a hair count is desired;
    cutting the hair in the area so identified, the hair being cut such that it can be viewed in its entirety at its exit from the skin by a viewing instrument;
    viewing the cut area of the skin through an aperture in the viewing instrument; and
    counting the hairs in the aperture to determine the hair count in the aperture.

2. A method according to claim 1, wherein the viewing instrument includes an adjustable focal length lens, and further comprising the step of adjusting the focus of the lens to view the area of the aperture and the hair contained therein.

3. A method according to claim 1, wherein the size of the aperture is variable, and further comprising the step of varying the aperture to a known surface area.

4. A method according to claim 1, further comprising the step of illuminating the area within the aperture by a light source.

5. A method according to claim 4, wherein the light source is external to the viewing instrument.

6. A method according to claim 4, wherein the light source is internal to the viewing instrument.

7. A method according to claim 5 or 6, wherein the light source does not directly illuminate the cut area.

8. A method according to claim 1, wherein the size of the aperture is variable, and further comprising the steps of varying the aperture and measuring the surface area of the aperture.

9. An apparatus for measuring hair density, said apparatus being applyable to an area of skin prepared to receive the apparatus, comprising:
    an optical magnifying lens having an adjustable focal length;
    a housing container for the optical magnifying lens, said housing container having an aperture positioned for viewing from the lens wherein the focal length of the lens is adjustable so as to permit viewing of the aperture from the lens; and
    means for counting hairs viewable through the aperture.

10. An apparatus according to claim 9, further comprising means for adjusting the focal length of a lens to view the area of skin.

11. An apparatus according to claim 9, further comprising means for measuring the area of the aperture.

12. An apparatus according to claim 9, further comprising means for counting hairs viewable in the aperture.

13. An apparatus according to claim 9, further comprising mirrors or sets of mirrors for viewing the aperture from different perspectives.

14. An apparatus according to claim 9, further comprising a light source contained in the housing container for illuminating the area of the aperture.

15. An apparatus according to claim 14, wherein said light source does not directly illuminate the cut area.

16. An apparatus according to claim 9, further comprising means for recording an image of hairs viewable in the aperture.

17. An apparatus according to claim 16, wherein said means for recording includes a camera.

* * * * *